United States Patent [19]
Kim et al.

[11] Patent Number: 5,539,110
[45] Date of Patent: Jul. 23, 1996

[54] METHOD FOR THE PREPARATION OF (−)PIPERAZINE BENZOXAZINE DERIVATIVES

[75] Inventors: Youseung Kim; Soon Bang Kang; Seonhee Park, all of Seoul, Rep. of Korea

[73] Assignee: Korea Institute of Science and Technology, Rep. of Korea

[21] Appl. No.: 321,360

[22] Filed: Oct. 11, 1994

[30] Foreign Application Priority Data

Mar. 22, 1994 [KR]  Rep. of Korea ............... 5762/1994

[51] Int. Cl.[6] ............................................. C07D 498/06
[52] U.S. Cl. ...................................................... 544/101
[58] Field of Search .............................................. 544/101

[56] References Cited

U.S. PATENT DOCUMENTS 5,237,060   8/1993   Schriewer et al. ................. 544/101

OTHER PUBLICATIONS

Hayakawa et al., "Synthesis an antibacterial Activities of Substituted 7–Oxo–2, 3–dihydro–7H–pyrido–[1,2,3,–de][1,4] benzoxazine–6–carboxylic Acids", *Chem. Pharm. Bull.*, 32:4907–4913 (1984).

Schriewer et al., "Preparation of Chiral–bridged Quinolone Bactericides, including S–Ofloxacin", *Chem. Abstr.* 107:154342c (1987).

Mitscher et al., "Chiral DNA Gyrase Inhibitors. 2. Asymmetric Synthesis and Biological Activity of the Enantiomers of 9–Fluoro–3–methyl–10–(4–methyl–1–piperazinyl)–7–oxo–2,3–dihydro–7H–pyrido[1,2,3–de]–1,4–benzoxazine–6–carboxylic Acid (Ofloxacin)", *J. Med. Chem.*, 30:2283 (1987).

"Levofloxacin", *Drugs of the Future* 17:559–563 (1992).
Masuzawa, Chemical Abstract 108: 112468p (1988).
Egawa, Chemical Abstract 108: 167489b (1988).

*Primary Examiner*—Philip I. Datlow
*Attorney, Agent, or Firm*—Townsend and Townsend and Crew

[57] ABSTRACT

There is disclosed a method for the preparation of the antibacterial (−) piperazine benzoxazine derivative having formula I comprising the steps of reacting (+)2-aminomethylene-3-oxo-3-phenylpropionate derivative of formula II with a base in an organic polar solvent, to give a (−) benzoxazine derivative of formula III: and reacting the (−) benzoxazine derivative of formula III with a piperazine derivative of formula IV in an organic polar solvent.

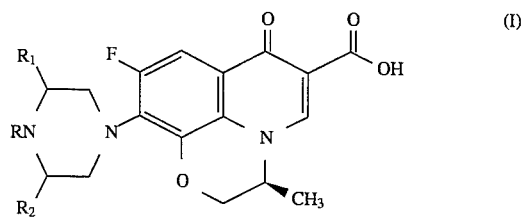

(I)

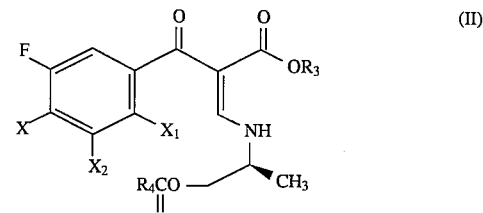

(II)

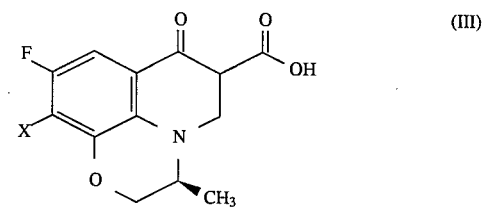

(III)

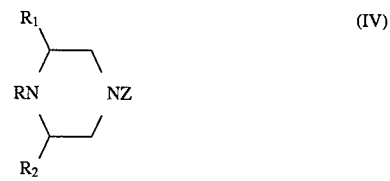

(IV)

10 Claims, No Drawings

METHOD FOR THE PREPARATION OF (−)PIPERAZINE BENZOXAZINE DERIVATIVES

BACKGROUND OF THE INVENTION

1. Field of the invention

The present invention relates to a novel method for the preparation of (−)9-fluoro-7-oxo-2,3-dihydro-7H-pyrido[1,2,3-de]-1,4-benzoxazine-6-carboxylic acid derivatives having antibacterial activity and pharmaceutically acceptable salts thereof.

2. Description of the Prior Art

According to literature (Drugs of the Future 1992, 17(2), pp 559–563), it is reported that the (−) piperazine benzoxazine derivatives have a potent antibacterial activity for a wide range of bacteria.

Preparation methods for the antibacterially active compound of the formula I, one of (−)piperazine benzoxazine derivatives, are disclosed in many patents, for example, Japanese Patent Nos. 87215591 and 87198685 and European Patent No. 225552.

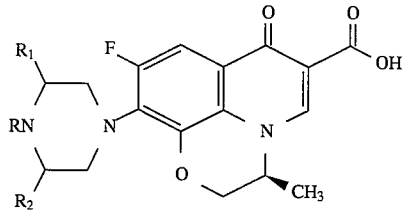

wherein R, $R_1$ and $R_2$ each is a hydrogen or a $C_1$–$C_4$ alkyl group.

These conventional methods, however, are disadvantageous in many aspects. For example, the reaction procedure employed in the conventional methods is carried out in 8 tedious steps, and a production yield is low. Further, the conventional methods use an isomer separation technique, which is unsuitable for industrial mass production.

SUMMARY OF THE INVENTION

It is, therefore, an object of the present invention to provide a novel method for the preparation of (−)9-fluoro-7-oxo-2,3-dihydro-7H-pyrido[1,2,3-de]-1,4-benzoxazine-6-carboxylic acid derivative.

The method in accordance with the present invention is advantageous in respect of shortening the procedure steps, improving in production yield, and being suitable for mass production.

In accordance with the present invention, the above object could be accomplished by providing a method for the preparation of (−) piperazine benzoxazine derivative having the following formula I:

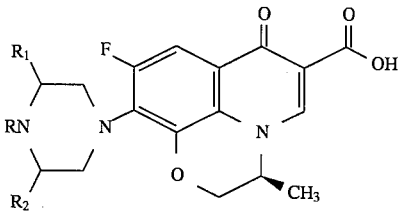

wherein R, $R_1$ and $R_2$ each is a hydrogen or a $C_1$–$C_4$ alkyl group, comprising the steps of:

reacting a (+)2-aminomethylene-3-oxo-3-phenylpropionate derivative of the following formula II:

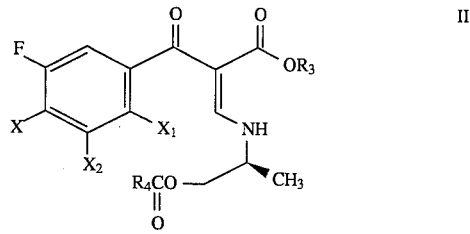

wherein $R_3$ and $R_4$ each is a $C_1$–$C_4$ alkyl group, and X and $X_1$ each is a halogen or nitro group, and $X_2$ is a halogen, with a base in an organic polar solvent, to give a (−) benzoxazine derivative of the following general formula III:

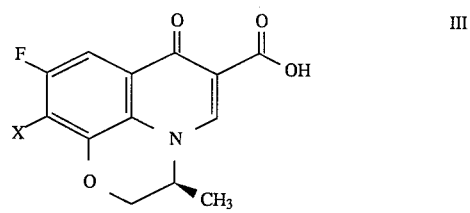

wherein X is defined as above; and reacting the (−) benzoxazine derivative of formula III with a piperazine derivative of the formula IV:

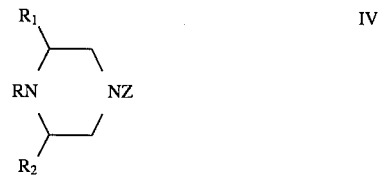

wherein R, $R_1$ and $R_2$ are defined as above, and Z is a hydrogen or trialkylsilyl group in which alkyl is a lower alkyl such as methyl, ethyl, butyl or t-butyl, in an organic polar solvent.

These and other objects and advantages of the present invention will become more apparent as the following description proceeds.

DETAILED DESCRIPTION OF THE INVENTION

In accordance with the present invention, (−) 9-fluoro-7-oxo-2,3-dihydro-7H-pyrido[1,2,3-de]-1,4-benzoxazine-6-carboxylic acid derivatives of formula I, antibacterially active compounds, can be prepared from a novel compound of formula II through an intermediate of formula III, also a novel compound.

In order to help understand the present invention, the preparation method of the present invention is summarized in the following reaction scheme:

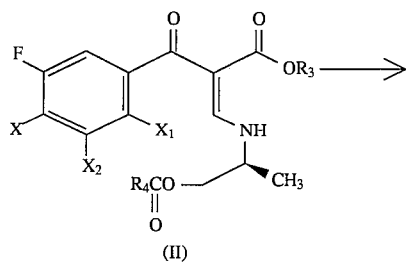

(II)

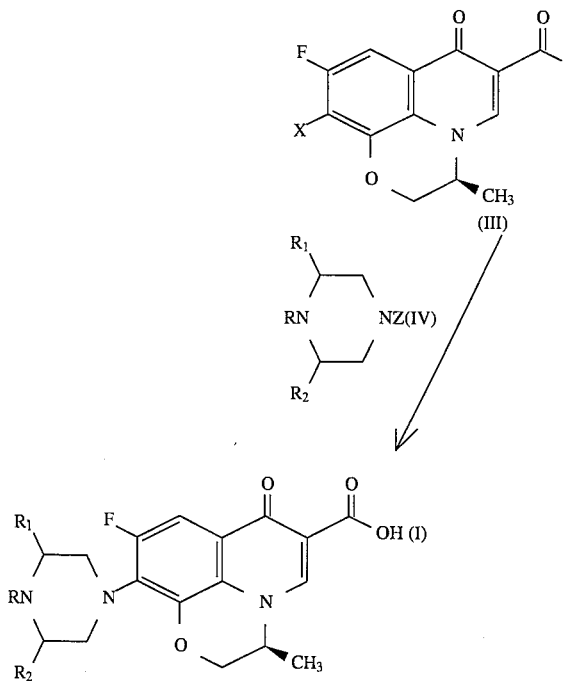

The compound of formula II, starting material for the synthesis of the compound of formula I, and its preparation method are described in detail in Korean Patent Application No. 5761/94 of the present inventors, filed on 22 Mar. 1994 (counterpart U.S. patent application Ser. No. 08/321,359 filed Oct. 11, 1994). This compound can be prepared from (S)-(+)-2-amino-1-propanol through 3 steps, according to the just mentioned application which is incorporated herein by reference. The compounds of formula II can be obtained by reacting alkyl propiolate of the following formula V

 V wherein $R_3$ is an alkyl containing 1 to 4 carbon atoms, with (S)-(+)-2-amino-1-propanol of the following formula VI

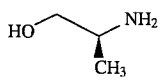 VI in an organic solvent, to give a (+) acrylate derivative of the following formula VII

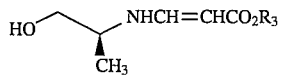 VII wherein $R_3$ is as defined hereinabove;
treating the (+) acrylate derivative of formula VII with an acyl chloride derivative of the following formula VIII

 VIII wherein $R_4$ is an alkyl containing 1 to 4 carbon atoms, in the presence of a suitable base, to give a (+) alkylacrylate derivative of the following general formula IX

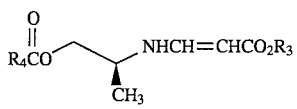 IX wherein $R_3$ and $R_4$ are as defined hereinabove; and
treating the (+) alkylacrylate derivative of formula IX with a benzoyl derivative of the following formula X

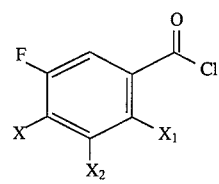 X wherein X is a halogen; and $X_1$ and $X_2$ are independently selected from a halogen and nitro, in the presence of a suitable base.

In order to help understand the present invention, the preparation method of the present invention is summarized in the following scheme.

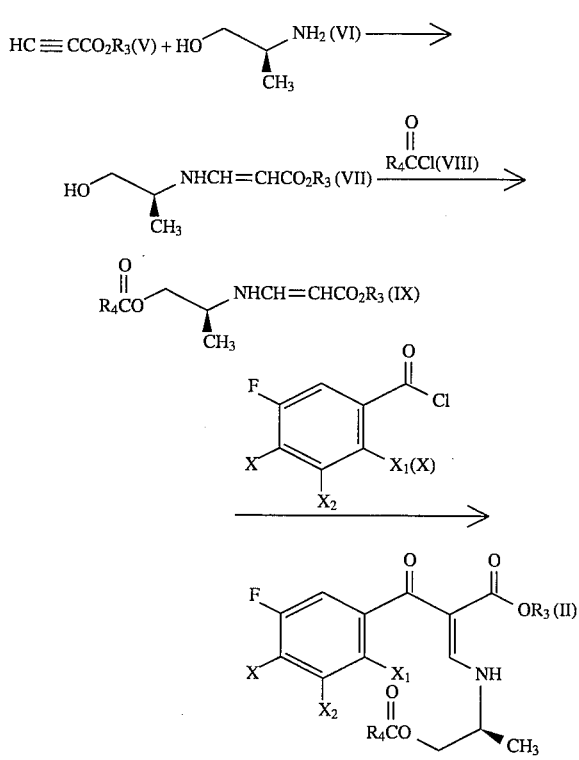

In accordance with a further as of the present invention, a compound of formula VII, an intermediate useful to prepare the compound of formula II is provided.

In accordance with still a further aspect of the present invention, a compound of formula IX, another intermediate useful to prepare the compound of formula II is provided.

The organic solvent effective for the reaction of the compound of formula V with (S)-(+)-2-amino-1-propanol of formula VI includes acetonitrile, tetrahydrofuran, dimethylformamide, dioxane, dimethylacetamide, dimethylsulfoxide, chloroform, methylenechloride, ethylenechloride or diethylether. In the organic solvent, this reaction is carried out at a temperature of 0° to 25° C. for 1 to 10 hrs. In the reaction, the equivalent ratio of the compound of formula V to the compound of formula VI is preferably 1:1.

In an organic solvent, such as acetonitrile, tetrahydrofuran, methylene chloride, diethylether, ethylene chloride and chloroform, the compound of formula VII is stirred along with the compound of formula VIII at a temperature of 0° to 20° C. for 10 minutes to 2 hrs in the presence of the above-mentioned base, so as to give a (+)alkylacrylate derivative of formula IX, a novel compound. In this reaction, the equivalent ratio of the compound of formula VII to the compound of formula VIII to the base is preferably in the range of 1:1.1:1.1 to 1:1.1:1.5.

While being heated, the (+) alkylacrylate derivative of formula IX is stirred along with benzoyl chloride of formula X in an organic solvent, such as acetonitrile, dimethylformamide, dimethylacetamide, tetrahydrofuran, dimethylsulfoxide, methylene chloride, chloroform and diethylether, at a temperature of 0° to 100° C. for 10 minutes to 2 hrs in the presence of base to yield (+)2-benzoyl-3-[(prop-2(S)-yl)amino]acrylate derivatives of formula II.

In this reaction, the equivalent ratio of the compound of formula IX to the compound of formula X to the base is preferably in the range of 1:1.1:1.2 to 1:1.2:1.5.

As a preferred base for the present invention, triethylamine, pyridine, potassium carbonate, sodium carbonate, calcium carbonate, 4-dimethylaminopyridine, 1,8-diazabicyclo[5.4.0]undec-7-en or 1,5-diazabicyclo[4.3.0]non-5-en can be used.

The products of those reactions including (+)2-benzoyl-3-[(prop-2(S)-yl)amino]acrylate derivatives of formula II, the (+) alkylacrylate derivative of formula VII and the (+) alkylacrylate derivative of formula IX can be separated and purified by conventional techniques, such as evaporation, filtration, extraction, chromatography, distillation and the combinations thereof. For example, the mixture containing the product is initially dried under reduced pressure to condense it. The resultant residue is mixed with a mixture of water and an organic solvent, such as ethylene chloride, chloroform, diethylether or ethylacetate, and then the organic solvent is condensed to give a product. In case of the mixture of product and by-products, further purification may be performed by chromatography, re-distillation or recrystallization.

Unless otherwise stated, all percentages, parts and ratios therein are by weight.

A. Preparation of Intermediates

EXAMPLE 1

(+) Ethyl 3-[(1-hydroxyprop-2(S) -yl)amino]acrylate (VII: $R_3$=ethyl).

3.76 g (50 mmol) of (+)-2-amino-1-propanol (VI) was added in 80 ml of acetonitrile and cooled to 0° C. To this, 5.07 ml (50 mmol) of ethyl propiolate (V, $R_3$=ethyl) was slowly added dropwise. The reactant mixture was stirred at a temperature not more than 5° C. for 8 hours and further stirred at room temperature for 1 hour.

Thereafter, the solvent was removed under reduced pressure (25° C./10 mmHg), to give 8.57 g of a colorless oily product (yield 99%).

Analysis of the product revealed that Z and E isomers were present in a ratio of 7:3 therein.

$IR_4$ (KBr) $cm^{-1}$: 3330, 1660, 1600.

$[\alpha]^{20}_{589}$: +56.6° C. ($CHCl_3$, C=0.242).

NMR($CDCl_3$) ppm: 7.65–7.82(1H×7/10, m), 7.50(1H×3/10, dd, J=13.3, 9.3H), 6.74(1H×7/10, dd, J=13.1, 8.1H), 4.82–4.88(1H×3/10, m), 4.78(1H×3/10, d, J=13.3H), 4.50(1H×7/10, d, J=8.1H), 4.10–4.12(2H, q, J=7H), 3.41–3.72(2H, m), 3.26–3.40(1H m), 2.36(1H, brs), 1.25–1.26(3H, t, J=7H), 12.0(3H, d, J=6.8H).

EXAMPLE 2

(+)Ethyl 3-[(1-acetoxyprop-2(S)-yl)amino]acrylate (IX: $R_4$=methyl, $R_3$=ethyl).

3.46 g (20 mmol) of (+)ethyl 3-[(1-hydoxyprop-2(S)-yl)amino]acrylate, 3.21 ml (23 mmol) of triethylamine and 0.244 g (2 mmol) of 4-dimethylaminopyridine were added in 50 ml of methylenechloride and cooled to 0° C. To this solution, 1.51 ml (22 mmol) of acetylchloride (VIII, $R_4$=methyl) was slowly added dropwise. The reactant mixture was stirred for 30 minutes and then, the precipitate was filtered off.

Thereafter, the filtrate was washed with 5 ml of aqueous 0.2N hydrochloric acid solution, 5 ml of aqueous sodium bicarbonate solution, and 5 ml of saturated saline water, in due order and then dried over magnesium sulfate. The organic solvent was completely removed under reduced pressure (25° C. C/20 mmHg), to give 4.22 g of an oily product (yield 98%).

Analysis of the product revealed that Z and E isomers were present in a ratio of 4:1 therein.

IR (NaCl) $cm^{-1}$: 3332, 1740, 1670, 1610.

$[\alpha]^{20}_{589}$:+65.31° C. ($CHCl_3$, C=0.222).

NMR ($CDCl_3$) ppm: 7.69–7.87(1H×3/4, m), 7.44(1H×1/4, dd, J=13.9H), 6.67(1H×3/4, dd, J=13.8H), 4.85–4.95(1H× 1/4, m), 4.79(1H×1/4, d, J=13H), 4.50(1H×3/4, d, J=8H), 4.11(2H, q, J=7H), 3.95–4.06(2H, m), 3.42–3.53(1H, m), 2.08(3H, s), 1.26(3H, t, J=7H).

B. Preparation of the Product

EXAMPLE 3

(+)Ethyl 2-[2,3,4,5-tetrafluoro)benzoyl-3-[(1-acetoxyprop-2(S)-yl)amino]acrylate (II: $R_4$=methyl, $R_3$=ethyl, $X,X_1$, $X_2$,=fluoro).

1.08 g (5 mmol) of (+)ethyl 3-[1-acetoxyprop-2(S)-yl)amino]acrylate and 0.77 ml (5.5 mmol) of triethylamine were added in 40 ml of acetonitrile and cooled to 0° C. To this solution, 1.12 g (5.25 mmol) of 2,3,4,5-tetrafluorobenzoyl chloride (X, X, $X_1$, $X_2$=fluoro) was slowly added dropwise. The reactant mixture was stirred for 30 minutes and then, the precipitate was filtered off.

Thereafter, the solvent was removed under reduced pressure (25° C./20 mmHg), to leave the residue which was subsequently added in 50 ml of methylene chloride and washed with 5 ml of aqueous saturated ammonium chloride solution, 5 ml of aqueous saturated sodium bicarbonate solution and 5 ml of saline water, in due order.

The solvent was dried over magnesium sulfate and removed completely under reduced pressure (25° C./20 mmHg), to give 1.90 g of an oily product (yield 97%).

Analysis of the product revealed that cis and trans isomers were present in a ratio of 3:1 or 1:3 herein.

IR (NaCl) $cm^{-1}$: 3230, 1740, 1700, 1620, 1560.

$[\alpha]^{20}_{589}$: +61.4° C. ($CHCl_3$, C=0.412).

NMR (CDCl$_3$) ppm: 9.39–10.95 (1H, brs), 8.13 and 8.16(1H, d), 7.08–7.16(1H×1/4, m), 6.96–7.04(1H×3/4, m), 4.04–4.24(2H, m) 4.04–4.08(2H, t, J=7H), 3.74–3.88(1H, m), 2.13(3H, s), 1.39 and 1.42(3H, d), 1.11(3H×3/4, t, J=7H), 0.98(3H×1/4, J=7H).

EXAMPLE 4

(+) Ethyl2-(2-nitro-3,4,5-trifluoro)benzoyl-3-{(1-acetoxyprop-2(S)-yl)amino]acrylate (II; $R_4$=methyl, $R_3$=ethyl, X, $X_2$=fluoro, $X_1$=nitro).

1.08 g (5 mmol) of (+)ethyl 3-[1-acetoxyprop-2(S)-yl)amino]acrylate and 0.78 ml (5.5 mmol) of triethylamine were added in 40 ml of acetonitrile and cooled to 0° C. To this solution, 2-nitro-3,4,5-trifluorobenzoyl chloride (X: X, $X_1$=fluoro, $X_2$=nitro) was slowly added dropwise. This reactant mixture was stirred for 30 minutes and then, a filtration procedure was carried out in the same manner with that of Example 3, to give 2.04 g of an oily product (yield 98%).

Analysis of the product revealed that cis and trans isomers were present in a ratio of 7:2 or 2:7 therein.

IR (KBr) cm$^{-1}$: 1740, 1700, 1640, 1550. $[\alpha]^{20}_{589}$: +72.14 ° C. (CHCl$_3$, C=0.384)

NMR (CDCl$_3$) ppm: 9.54–10.91(1H, brs), 8.26(1H×2/9, d, J=14.8H), 8.17(1H×7/9, d, J=14H), 6.91–7.02(1H, m), 4.03(2H, q, J=7H), 3.94–4.25(2H, m), 3.78–3.86(1H, m), 2.13(3H, s), 1.40–1.43(3H, m), 1.12(3H×7/9, t, J=7H), 0.93(3H×2/9, t, J=7H).

As shown in the reaction scheme, the method of the present invention comprises two steps.

In the first step, (+) 2-aminomethylene-3-oxo-3-phenylpropionate derivative of formula II along with a base is stirred at a temperature ranging from 0° to 150° C. for 1 to 10 hours in an organic polar solvent and then, after addition of water, further stirred at a temperature ranging from 25° to 150 ° C. for 1 to 10 hours, so as to give a benzoxazine derivative of formula III, an intermediate.

A base suitable to react with the novel. Compound of formula II may be selected from a group consisting of metal hydroxides, metal hydrides and metal carbonates. Preferred metal hydroxides include calcium hydroxide, sodium hydroxide, potassium hydroxide and lithium hydroxide. Preferred metal hydrides include calcium hydride, sodium hydride, potassium hydride and lithium hydride. Preferred metal carbonates include potassium carbonate, sodium carbonate, lithium carbonate and barium carbonate.

The equivalent ratio of the compound of formula II to the base is preferably in a range of from 3 to 6.

In case of employing metal hydroxide or metal carbonate as the base, a mixture of an organic polar solvent and water (in a volume ratio of 2:1 to 3:1) may be used for the fist reaction step. However, it is preferred that the reaction of the compound of formula II with the base is initially carried out in the organic polar solvent and then, water is added.

The organic solvent suitable to carrying out the reaction of the novel compound of formula II with the base is selected from a group consisting of acetonitrile, dimethyl acetamide, sulfolane, dimethyl sulfoxide, dimethylformamide, tetrahydrofuran, dioxane and pyridine.

In the compound of formula II used as a starting material for the synthesis of the compound of formula I, the compounds II wherein $X_1$ and $X_2$ each is a fluoro, a chloro or a nitro group, and X is a fluoro or chloro are most preferable.

In the second step of the method according to the present invention, the benzoxazine derivative of formula III is reacted with the piperazine derivative of the formula IV by stirring both derivatives in an organic polar solvent at a reaction temperature of about 50° to about 150 ° C. for 2 to 24 hours, to give the (–) piperazine benzoxazine derivative of formula I. It is preferred that the equivalent ratio of the benzoxazine derivative of formula III to the piperazine derivative of formula IV is in a range of from 2 to 5 in this second step.

Organic polar solvent suitable to perform the second reaction step is selected from a group consisting of pyridine, dimethyl sulfoxide, acetonitrile, dimethyl formamide, N-methylpyrrolidone and sulforane.

In the case that the piperazine derivative of formula IV wherein Z is a trimethyl silane group is used in the second step, tetraalkyl ammonium fluoride or a mixture of tetraalkyl ammonium halide and metal fluoride may be added so as to remove the trimethyl silane group from the piperazine derivative.

Where tetraalkyl ammonium fluoride or the mixture of tetraalkyl ammonium halide and metal fluoride is added, the equivalent ratio of the benzoxazine derivative of formula III to the piperazine derivative of formula IV is preferably in a range of 1 to 3. The equivalent ratio of the benzoxazine of formula III to the tetraalkyl ammonium fluoride is preferably in a range of 1 to 1.2. It is preferred that the tetraalkyl halide is mixed with the metal fluoride in an equivalent ratio of about 1:2.

Tetraalkyl ammonium fluoride useful to the present invention include tetramethylammonium fluoride, tetraethyl ammonium fluoride and tetrabutyl ammonium fluoride.

With regard to tetraalkyl ammonium halide, tetramethyl ammonium chloride, tetraethyl ammonium chloride, tetrabutyl ammonium chloride, tetramethyl ammonium bromide, tetrapropyl ammonium bromide, tetrabutyl ammonium bromide, tetrapentyl ammonium bromide, tetramethyl ammonium iodide, tetraethyl ammonium iodide, tetrapropyl ammonium iodide and tetrabutyl ammonium iodide and tetrapentyl ammonium iodide is useful in the present invention.

Metal fluoride useful in the present invention is selected from a group consisting of cesium fluoride, potassium fluoride, calcium fluoride and sodium fluoride.

The antibacterially active compounds of formula I can be prepared in only two reaction steps, according to the present invention, which results in high production yield. Consequently, the method of the present invention is very advanced and economical compared to the conventional methods, having complicated multi-reaction steps and unsuitable for industrial application.

The prepared compound of formula I may be reacted with an organic acid such as methane sulfonic acid and p-toluene sulfonic acid or an inorganic acid such as hydrochloric acid and sulfuric acid, so as to produce an acid addition salt. Also, it may be reacted with sodium or potassium, to give a corresponding carboxylic acid salt.

Products obtained by the method of the present invention may be separated and filtered in a conventional manner such as evaporation, filtration, extraction, recrystallization and the combination thereof. For example, reaction mixture is cooled to room temperature to obtain a precipitate which is subsequently filtered. Thereafter, the solvent used is removed by concentration. To the concentrate, water is added to precipitate a product and filtered to collect the product. When a by-product is included, the product may be further purified by washing, chromatography or re-crystallization.

The preferred embodiments of the present invention will now be further described with reference to specific examples. Unless otherwise stated, all percentages, parts and ratios therein are by weight.

EXAMPLE 5

(−)9,10-Difluoro-2,3-dihydro-3(S)-methyl-7-oxo-7H-pyrido[1,2,3-de]-1,4-benzoxazine-6-carboxylic acid (III, X=F)

1.69 g (4.32 mmol) of (+) ethyl 2-(2,3,4,5-tetrafluoro)benzoyl-3-[(1-acetoxy-prop-2(S)-yl)amino]acrylate (II: X, $X_1$, $X_2$=fluoro, $R_3$=ethyl, $R_4$=methyl) was added to 30 ml of tetrahydrofuran and cooled to 0° C. This solution was added with 1.21 g (21.6 mmol) of potassium hydroxide and then stirred at room temperature for 1 hour. To this, 15 ml of water was added and stirred for 2 hours under heat. After being cooled to room temperature, the reaction mixture was filtered to remove undissolved substances. The filtrate was removed under reduced pressure (25° C./10 mmHg) and 50 ml of water was added. The resulting aqueous solution was washed with 10 ml of methylene chloride once and then, cooled to 0° C. 1N HCl solution was slowly added, to adjust the pH of the aqueous solution to pH 2. Filtration was carried out to obtain a solid which was, in turn, washed with 5 ml of water and 5 ml of a mixed solution of ethanol and ethyl ether (volume ratio 1:4) and then, dried, to give 0.98 g of a solid product (yield 81%).

m.p. :284°–286° C. (dec.)

IR (KBr) cm$^{-1}$: 1720, 1620

$[\alpha]^{20}_{589}$: −41.8° C. (CHCl$_3$, C=0.091)

NMR(TFA-d$_1$) ppm: 9.39(1H, s), 8.10(1H, t, J=8H), 5.11–5.26(1H, m), 4.65–4.79(2H, m), 1.82(3H, d, J=6.7H).

EXAMPLE 6

(−) 9,10-Difluoro-2,3-dihydro-3(S)-methyl-7-oxo-7H-pyrido[1,2,3-de]-1,4-benzoxazine-6-carboxylic acid (III: X=F)

1.52 g (3.6 mmol) of (+) ethyl 2-(2-nitro-3,4,5-trifluoro)benzoyl-3-[(1-acetoxy-prop-2(S)-yl)amino]acrylate (II: $X_1$=nitro, X, $X_2$=fluoro, $R_3$=ethyl, $R_4$=methyl) was added to 30 ml of tetrahydrofuran and cooled to 0° C. To this, 1.01 g (18 mmol) of potassium hydroxide was added and stirred at room temperature for 30 minutes. The resulting reaction mixture was added with 15 ml of water and stirred for 2 hours under heat. Filtering procedure was carried out in the same manner as that of Example 5, to give 0.86 g of solid product (yield 84%).

m.p.: >280° C.

EXAMPLE 7

(−) 9,10-Difluoro-2,3-dihydro-3(S)-methyl-7-oxo-7H-pyrido[1,2,3-de]-1,4-benzoxazine-6-carboxylic acid (III: X=fluoro)

0.86 g (2.1 mmol) of (+) ethyl 2-(2-nitro-3,4,5-trifluoro)benzoyl-3-[(2-acetoxy-1(S)-methyl)amino]acrylate (II: $X_1$=nitro, X, $X_2$=fluoro, $R_3$=ethyl, $R_4$=methyl) was added to 20 ml of dioxane and cooled to 0° C. To this, 74 mg (2.5 mmol) of sodium hydride mixed with mineral oil (purity 80%) was added and stirred at room temperature for 2 hours. After being cooled to 0° C., the resulting reaction mixture was added with 20 ml of water and 0.46 g (8.4 mmol) of potassium hydroxide. Filtration was carried out for 3 hours, to give 0.48 g of solid product (yield 83%).

m.p. :>280° C.

EXAMPLE 8

(−) 9,10-Difluoro-2,3-dihydro-3(S)-methyl-7-oxo-7H-pyrido[1,2,3-de]-1,4-benzoxazine-6-carboxylic acid (III: X=fluoro)

1.20 g (3.1 mmol) of (+) ethyl 2-(2,3,4,5-tetrafluoro)benzoyl-3-[(1-acetoxy-prop-2(S)-yl)amino]acrylate (II: X, $X_1$, $X_2$=fluoro, $R_3$=ethyl, $R_4$=methyl) was added to 20 ml of dimethylformamide and subsequently added with 1.0 g (17.9 mmol) of potassium carbonate. After being stirred for 1 hour under heat, the reaction mixture was added with 20 ml of water and refluxed for 3 hours under heat. The resulting solution was cooled and then, filtered in the same manner as that of Example 5, to give 0.39 g of solid product (yield 46%)

m.p.: >280° C.

EXAMPLE 9

(−)-9-Fluoro-3(S)-methyl-10-(4-methyl-1-piperazinyl-7-oxo-2,3-dihydro-7H-pyrido[1,2,3-de]-1,4-benzoxazine-6-carboxylic acid (I: R=methyl, $R_1$, $R_2$=hydrogen)

94 mg (0.33 mmol) of (−) 9,10-difluoro-2,3-dihydro-3(S)-methyl-7-oxo-7H-pyrido-[1,2,3-de]-1,4-benzoxazine-6-carboxylic acid (III: X=fluoro) and 0.098 ml (0.87 mmol) of N-methylpiperazine (IV: Z=hydrogen, R=methyl, $R_1$, $R_2$=hydrogen) were added to 5 ml of pyridine and refluxed at 120° C. for 12 hours. The solvent used was removed under reduced pressure (50° C./10 mmHg), and the remaining substance was added to 10 ml of ethyl ether. The obtained solid was subjected to filtration, washed with 5 ml of ethyl ether two times, and dried, to give 0.11 g of brown solid product (yield 91%).

m.p. :209°–211° C. (dec.)

IR (NaCl) cm$^{-1}$: 3470, 1720, 1620, 1520

$[\alpha]^{20}_{589}$: −91.2° C. (CHCl$_3$, C=0.137)

NMR (CDCl$_3$) ppm: 8.62(1H, s), 7.70(1H, d, J=12.3H), 4.53–4.54(1H, m), 4.35–4.52(2H, m), 2.49–3.42(8H, m), 2.33(3H, s), 1.61(3H, d, J=6.6H)

EXAMPLE 10

(−)-9-Fluoro-3(S)-methyl-10-(4-methyl-1-piperazinyl-7-oxo-2,3-dihydro-7H-pyrido[1,2,3-de]-1,4-benzoxazine-6-carboxylic acid (I: R=methyl, $R_1$, $R_2$=hydrogen)

206 mg (0.73. mmol) of (−) 9,10-difluoro-2,3-dihydro-3(S)-methyl-7-oxo-7H-pyrido[1,2,3-de]-1,4-benzoxazine-6-carboxylic acid (III: X-fluoro) and 440 mg (2.19 mmol) of 4-(t-butyldimethylsilyl)-1-methylpiperazine (IV: Z=t-butyldimethylsilyl, R=methyl, $R_1$, $R_2$=hydrogen) were added to 5 ml of pyridine and heated to 60° C. To this reaction mixture, a solution prepared by solving 572 mg (2.19 mmol) of tetrahydrobutyl ammonium fluoride in 5 ml of pyridine was slowly added dropwise. This reaction system was heated to 80° C. for 2 hours and then, the reaction solvent used was removed under reduced pressure (60° C./10 mmHg). The remaining substance was added with 20 ml of chloroform. The obtained solid was subjected to filtration. The filtered solution was washed with 5 ml of brine and dried over magnesium sulfate. Solvent was completely removed under reduced pressure (20° C./20 mmHg), to give 0.24 g of solid product (yield 89%).

EXAMPLE 11

(−)-9-Fluoro-3(S)-methyl-10-(4-methyl-1-piperazinyl-7-oxo-2,3-dihydro-7H-pyrido[1,2,3-de]-1,4-benzoxazine-6-carboxylic acid (I: R=methyl, $R_1$, $R_2$=hydrogen)

102 mg (0.36 mmol) of (−) 9,10-difluoro-2,3-dihydro-3(S)-methyl-7-oxo-7H-pyrido[1,2,3-de]-1,4-benzoxazine-6-carboxylic acid (III: X-fluoro) and 217 mg( 1.08 mmol) of 4-(t-butyldimethylsilyl)-1-methylpiperazine (IV: Z=t-butyldimethylsilyl, R=methyl, $R_1$, $R_2$=hydrogen) were added to 5 ml of pyridine. To this reaction mixture, a solution prepared by solving 300 mg (1.08 mmol) of tetrahydrobutyl ammonium chloride and 203 mg (2.16 mmol) of potassium fluoride hydrate in 5 ml of pyridine was slowly added dropwise. This reaction system was heated to 80° C. for 2 hours and then, filtered in the same manner as that of Example 10, to give 120 mg of solid product (yield 87%).

EXAMPLE 12

(−)-9-Fluoro-3(S)-methyl-10-(1-piperazinyl)-7-oxo-2,3-dihydro-7H-pyrido[1,2,3-de]-1,4-benzoxazine-6-carboxylic acid (I: R, $R_1$, $R_2$=hydrogen)

84 mg (0.3 mmol) of (−) 9,10-difluoro-2,3-dihydro-3(S)-methyl-7-oxo-7H-pyrido[1,2,3-de]-1,4-benzoxazine-6-carboxylic acid (III: X=fluoro) and 64 mg (75 mmol) of piperazine (IV: Z-hydrogen, R, $R_1$, $R_2$=hydrogen) were added to 2 ml of pyridine and stirred at 100° C. for 12 hours. The solvent used was removed under reduced pressure (50° C./10 mmHg). The remaining substance was added with 5 ml of water and the obtained solid was filtered off. From the resulting filtered solution, water was removed under reduced pressure (5° C./10 mmHg). The resulting solid residue was washed with 5 ml of ethyl ether and a mixture of ethyl ether and ethanol (volume ratio 1:1) and dried, to give 86 mg of solid product (yield 83%).

IR (KBr) cm$^{-1}$: 3430, 1620, 1580

NMR(TFA-d$_1$) ppm: 10.0(1H, s), 8.06(1H, d, J=11, 3H), 5.10–5.18(1H, m), 4.6–4.81(2H, m), 3.71–4.0(8H, m), 1.83(3H, d, J=6.3H)

EXAMPLE 13

(−)-9-Fluoro-3(S)-methyl-10-(1-piperazinyl-7-oxo-2,3-dihydro-7H-pyrido[1,2,3-de]-1,4-benzoxazine-6-carboxylic acid (I: R, $R_1$, $R_2$=hydrogen)

108 mg (0.38 mmol) of (−) 9,10-difluoro-2,3-dihydro-3(S)-methyl-7-oxo-7H-pyrido[1,2,3-de]-1,4-benzoxazine-6-carboxylic acid (III: X=fluoro) and 150 mg (0.76 mmol) of 4-(t-butyldimethylsilyl)piperazine (IV: Z=t-butyldimethylsilyl, R, $R_1$, $R_2$=hydrogen) were added to 5 ml of pyridine and heated to 60° C. To this reaction mixture, a solution prepared by solving 198 mg (0.76 mmol) of tetrahydrobutyl ammonium fluoride hydrate in 5 ml of pyridine was slowly added dropwise. This reaction system was heated to 80° C. for 2 hours and then, filtered in the same manner as that of Example 10, to give 128 mg of solid product (yield 88%).

Other features, advantages and embodiments of the invention disclosed herein will be readily apparent to those exercising ordinary skilled in the an after reading the foregoing disclosures. In this regard, while specific embodiments of the invention have been described in considerable detail, variations and modifications of these embodiments can be effected without departing from the spirit and scope of the invention as described and claimed.

What is claimed is:

1. A method for the preparation of (−) piperazine benzoxazine derivative having the formula I:

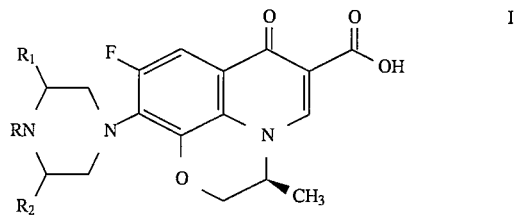

wherein R, $R_1$ and $R_2$ each is a hydrogen or a $C_1$–$C_4$ alkyl group, comprising the steps of:

reacting (+)2-aminomethylene-3-oxo-3-phenylpropionate derivative of the following formula II:

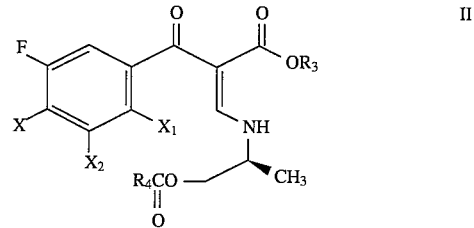

wherein $R_3$ and $R_4$ each is a $C_1$–$C_4$ alkyl group, and X and $X_1$ each is a halogen or nitro group, and $X_2$ is a halogen, with a base in an organic polar solvent, to give a (−) benzoxazine derivative of the following formula III:

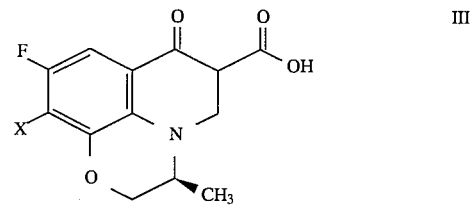

wherein X is defined as above; and reacting the (−) benzoxazine derivative of formula III with a piperazine derivative of the following formula IV:

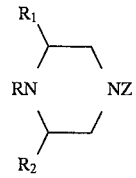

wherein R, $R_1$ and $R_2$ are defined as above, and Z is a hydrogen or trialkylsilyl group which alkyl is a $C_1$–$C_4$ alkyl group, in an organic polar solvent.

2. The method in accordance with claim 1, wherein the reaction of the (+)2-aminomethylene-3-oxo-3-phenylpropionate derivative of formula II with the base is carried out at a reaction temperature ranging from approximately 50° to approximately 150° C. for 2 to 24 hours.

3. The method in accordance with claim 1, wherein the reaction of the (−) benzoxazine derivative of formula III with the piperazine derivative of formula IV is carried out in the presence of tetraalkyl ammonium halide or a mixture of tetraalkyl ammonium halide and metal fluoride.

4. The method in accordance with claim 1, wherein the organic polar solvent used in the reaction of the (+)2-aminomethylene-3-oxo-3-phenylpropionate derivative of formula II with the base is selected from a group consisting of acetonitrile, dimethyacetamide, sulforane, dimethyl sulfoxide, dimethylformamide, tetrahydrofuran, dioxane and pyridine.

5. The method in accordance with claim 1, wherein the base is selected from a group consisting of metal hydroxide, metal carbonate and metal hydride.

6. The method in accordance with claim 5, wherein the metal hydroxide is selected from a group consisting of calcium hydroxide, sodium hydroxide, potassium hydroxide, barium hydroxide and lithium hydroxide.

7. The method in accordance with claim 5, wherein the metal carbonate is selected from a group consisting of potassium carbonate, sodium carbonate, lithium carbonate and barium carbonate.

8. The method in accordance with claim 5, wherein the metal hydride is selected from a group consisting of calcium hydride, sodium hydride, potassium hydride and lithium hydride.

9. The method in accordance with claim 1, wherein the organic polar solvent used in the reaction of the (−) benzoxazine derivative of formula III with the piperazine derivative of formula IV is selected from a group consisting of pyridine, dimethyl sulfoxide, acetonitrile, dimethylformamide, N-methyl pyrrolidone and sulforane.

10. The method in accordance with claim 3, wherein the tetraalkyl ammonium halide is selected from a group consisting of tetramethyl ammonium fluoride, tetraethyl ammonium fluoride, tetrabutyl ammonium fluoride, tetramethyl ammonium chloride, tetraethyl ammonium chloride, tetrabutyl ammonium chloride, tetramethyl ammonium bromide, tetrapropyl ammonium bromide, tetrabutyl ammonium bromide, tetrapentyl ammonium bromide, tetramethyl ammonium iodide, tetraethyl ammonium iodide, tetrapropyl ammonium iodide, tetrabutyl ammonium iodide and tetrapentyl ammonium iodide, and the metal fluoride is selected from a group consisting of cesium fluoride, potassium fluoride, calcium fluoride and sodium fluoride.

* * * * *